United States Patent [19]

Zajac, Jr.

[11] Patent Number: 5,189,228

[45] Date of Patent: Feb. 23, 1993

[54] TETRANITRONORADAMANTANE

[75] Inventor: Walter W. Zajac, Jr., Newton Square, Pa.

[73] Assignee: The United States of America as represented by the Secretary of the Army, Washington, D.C.

[21] Appl. No.: 905,711

[22] Filed: Jun. 29, 1992

Related U.S. Application Data

[63] Continuation of Ser. No. 718,323, Jun. 17, 1991, abandoned.

[51] Int. Cl.$^5$ ............................................... C07C 79/08
[52] U.S. Cl. ...................................... 568/941; 149/88
[58] Field of Search ........................... 149/88; 568/941

[56] References Cited

U.S. PATENT DOCUMENTS

| | | | |
|---|---|---|---|
| 3,006,971 | 10/1961 | Feuer et al. | 568/941 |
| 3,258,498 | 6/1966 | Schneiter | 568/941 |
| 3,535,390 | 10/1970 | Driscoll | 568/941 |
| 4,329,522 | 5/1982 | Gilbert et al. | 568/941 |
| 4,535,193 | 8/1985 | Sollitt et al. | 568/941 |
| 5,105,031 | 4/1992 | Zajac, Jr. | 568/941 |

OTHER PUBLICATIONS

Liebzon et al., Chem. Abs., 86, p. 567, abs. #86980llr (1977).

Primary Examiner—Edward A. Miller
Attorney, Agent, or Firm—Anthony T. Lane; Edward Goldberg; Edward F. Costigan

[57] ABSTRACT

3,7,9,9-Tetranitronoradamantane.

1 Claim, No Drawings

TETRANITRONORADAMANTANE

GOVERNMENTAL INTEREST

The Government has rights in this invention pursuant to Contract No. DAAK10-85-C-0075 awarded by Department of of the Army.

CROSS REFERENCE TO RELATED APPLICATION

This application is a continuation-in-part of application Ser. No. 07/718,323, filed Jun. 17, 1991, now abandoned.

FIELD OF USE

This invention relates to 3,7,9,9-Tetranitronoradamantane and a method of making the same.

BACKGROUND

It is well know that caged molecular structures, as they are known in the art, are highly energetic. They are strained at nearly every angle in their configuration. When they are nitrated, they yield compounds, which are highly useful in explosives, pyrotechnics, munitions and the like. Every addition of a nitro group onto such a structure can be considered a high contribution to the art of energetic material.

It is sometimes impossible to even consider an addition of anitro group to a strained structure for we don't know what to expect in the process of making such compound. The latter compound itself, which was made, is so far beyond what could be expected without incident.

SUMMARY OF INVENTION

It is an object of this invention to provide a new and highly energetic compound to the field of explosives; and a process of making it.

Another object is to make 3,7,9,9-Tetranitronoradamantane, and a process of making it.

PREFERRED EMBODIMENT

There are other nitro-cage compounds known in the art. The particular compound of this invention is related to the nitro-cage compounds set forth in U.S. copending application, Ser. No. 07/718,318, filed Jun. 17, 1991 and now U.S. Pat. No. 5,105,031, issued Apr. 14, 1992.

SPECIFIC EXAMPLE

A 100 mL round-bottomed flask containing 30-35 mL chloroform was cooled in a dry ice/acetone bath and saturated with ozone (blue color). With continual ozonation a solution of 3,7-dinitro-9-hydroxylaminonoradamantane [See U.S. 5105031] (0.52 gm, 2.14 mmol) in chloroform (25 mL) andethylacetate (5 mL) was added dropwise over a 15 min. period. Ozonation was continued another 10 min after-which the solvent was removed under reduced pressure to afford a white amorphous solid mp>300°. (0.4861 gm, 88%) IR(KBr, cm$^{-1}$) 1541. 50.3 mHz, $^{13}$C NMR (CDCl$_3$) 38.60, 43.69, 44.42, 83.02, 93.00, 93.54. Anal. Calcd for $C_9H_{11}N_3O_6$: C, 42.03; H, 4.31; N. 16.34. Found: C, 41.87; H, 4.09; N, 16.09.

3,7,9,9-Tetranitronoradamantane

The 3,7,9,9-Trinitronoradamantane produced above (0.2968 g, 1.154 mmol) was suspended in methanol (5 mL) and water (5 mL). Sodium hydroxide (0.1 gm, 2.5 mmol) was added. This solution was placed in a 10 mL addition funnel which was attached to a 100 mL-3-necked round bottomed flask which was fitted with magnetic stirrer and firestone valve for the source of nitrogen. Into the 100 mL round bottomed flask was added potassium ferricyanide (2.06 gm, 6.26 mmol), sodium nitrate (1.0 gm, 14.5 mmol) with water (20 mL) and ether (40 mL). The entire system was evacuated and filled with nitrogen. With rapid stirring, the alkaline solution was added dropwise over a 30 minute period under nitrogen. Stirring was continued another 90 min. where upon the mixture turned a darker orange-yellow.

The reaction mixture was worked up by pouring it into a 125 mL separatory funnel. The ether layer was collected while the yellow aqueous layer was extracted again with ether (2×40 mL). The combined ether layers were washed with water (1×25 mL), dried with anhydrous sodium sulfate and evaporated under reduced pressure to afford a white solid known as 3,7,9,9-Tetranitronoradamantane. (0.1175 gm, 34%). m.p. 283-5(dec. IR (cm$^{-1}$) 1542, 1457, 200 mHz $^1$H NMR (CDCl$_3$) 2.50(dd,J=18.0, 10.5, 4H), 3.0-3.2(m,6H) 50.3 mHz, C NMR (CDCl) 2.50(dd,J=18.0, 10.5, 4H), 3.0-3.2(m,6H) 50.3 mHz, $^{13}$C NMR (CDCl) 2.50(dd,j=18.0, 10.5, 4H), 3.0-3.2(m,6H 50.3 mHz, $^{13}$C NMR (CDCl$_3$) 43.30(d), 46.12(t), 93.14(s), 113.94(s). Anal. Calcd for $C_9H_{10}N_4O_8$: C, 35.77; H, 3.34; N, 18.54. Found: C, 37.06, H, 3.65; N, 18. 29.

What is claimed is:

1. 3,7,9,9-Tetranitronoradamantane.

* * * * *